United States Patent [19]

Chick et al.

[11] 4,242,460
[45] Dec. 30, 1980

[54] CELL CULTURE DEVICE

[76] Inventors: William L. Chick, 32 Willow Rd., Wellesley, Mass. 02181; Pierre M. Galletti, 36 Taber Ave.; Peter D. Richardson, 60 Sargent Ave., both of Providence, R.I. 02906; Georg Panol, 165 Shenandoah Rd., Warwick, R.I. 02886

[21] Appl. No.: 972,961

[22] Filed: Dec. 26, 1978

[51] Int. Cl.³ .............................................. C12M 3/00
[52] U.S. Cl. ............................................ 435/284; 3/1;
128/DIG. 3; 210/497.1; 210/321.1; 210/321.2;
210/645
[58] Field of Search ............... 435/283, 284, 285, 286,
435/240, 241, 1, 2; 210/21, 321 R, 321 A, 497.1;
128/DIG. 3; 3/1

[56] References Cited
U.S. PATENT DOCUMENTS

| Re. 24,822 | 5/1960 | Pallotta et al. ................ 435/285 X |
| 3,131,143 | 4/1964 | Ferrari et al. ..................... 210/22 |
| 3,388,803 | 6/1968 | Scott .................................. 210/321 |
| 3,489,647 | 1/1970 | Kolobow ...................... 435/283 X |
| 3,734,851 | 5/1973 | Matsumura ...................... 210/22 |
| 3,742,946 | 7/1973 | Grossman ................... 210/321 X |
| 3,821,087 | 6/1974 | Knazek et al. .................. 195/127 |
| 3,827,565 | 8/1974 | Matsumura ...................... 210/22 |
| 3,883,393 | 5/1975 | Knazek et al. .................. 195/1.8 |
| 4,061,141 | 12/1977 | Hyden et al. .............. 128/DIG. 3 |

FOREIGN PATENT DOCUMENTS 1027304 3/1978 Canada .

OTHER PUBLICATIONS

Chick et al., A Hybrid Artificial Pancreas, Trans. Amer. Soc. Artif. Int. Organ., vol. XXI, pp. 8–14, 1975.
Whittmore, et al., Effects of the Hybrid Artificial Pancreas in Diabetic Rats, Trans, Am. Soc. Artif. Intern. Organs, vol. XXIII, pp. 336–340, 1977.
Galletti et al., Le Pancreas Artificiel, Journéles de Diabétologie, pp. 15–19, 1977.
Chick et al., Science, vol. 197, pp. 780–782; 1977.
Whittmore, Chick et al., Function of Hybrid Artificial Pancreas in Diabetic Rats, Surgical Forum, vol. XXVIII, pp. 93–97, 1977.
Chick, Like et al., Science, vol. 187, pp. 847–849, 1975.
Tanishita et al., Trans. Amer. Soc. Artif. Int. Organs, vol. XXI, pp. 216–223, 1975.

Primary Examiner—Robert J. Warden

[57] ABSTRACT

A cell culture device for use, e.g., as an artificial pancreas, featuring, in various aspects, a semipermeable tube wrapped about a spool and mounted within a cylinder to form a cell culture compartment; an inlet and an outlet strand of the semipermeable tube being wrapped to form alternating adjacent coils to provide improved convective transport; and the semipermeable tube being wrapped to form helical coils to provide improved conductive transport.

18 Claims, 7 Drawing Figures

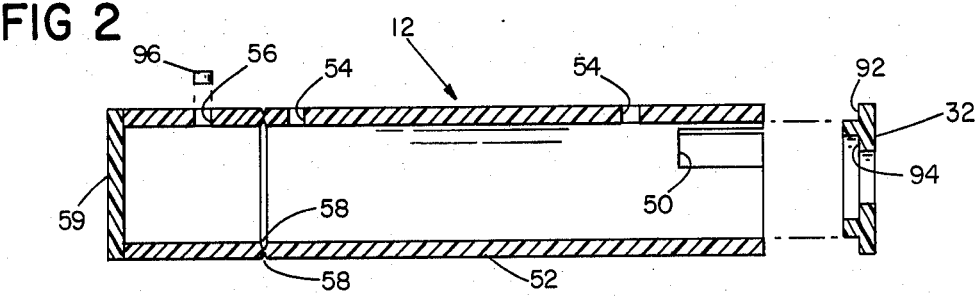
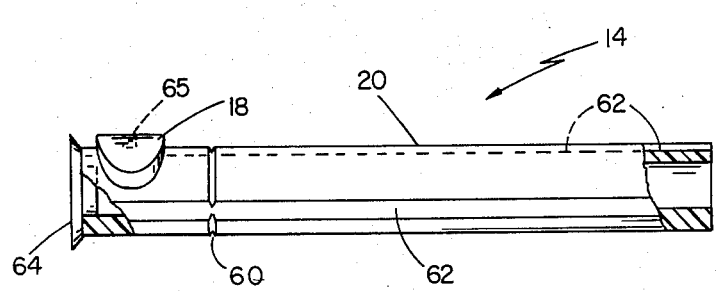
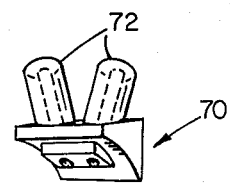
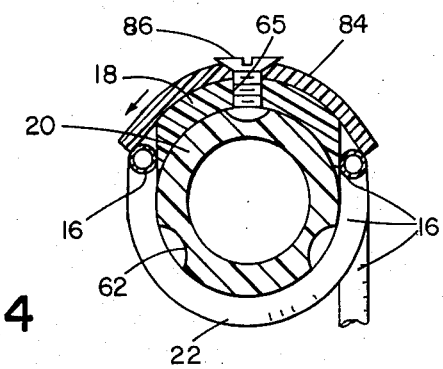
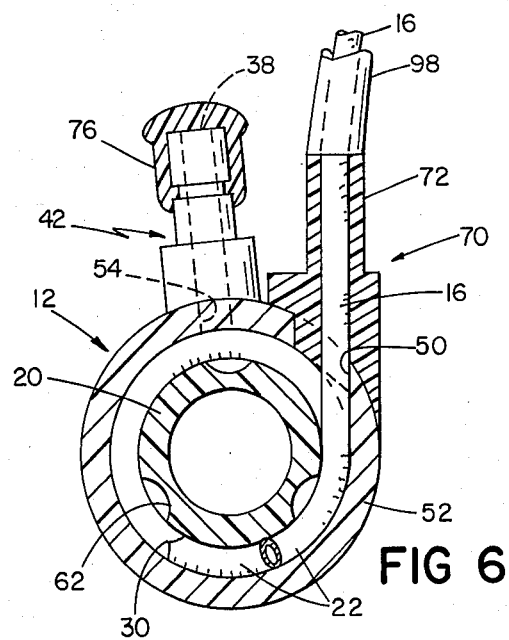
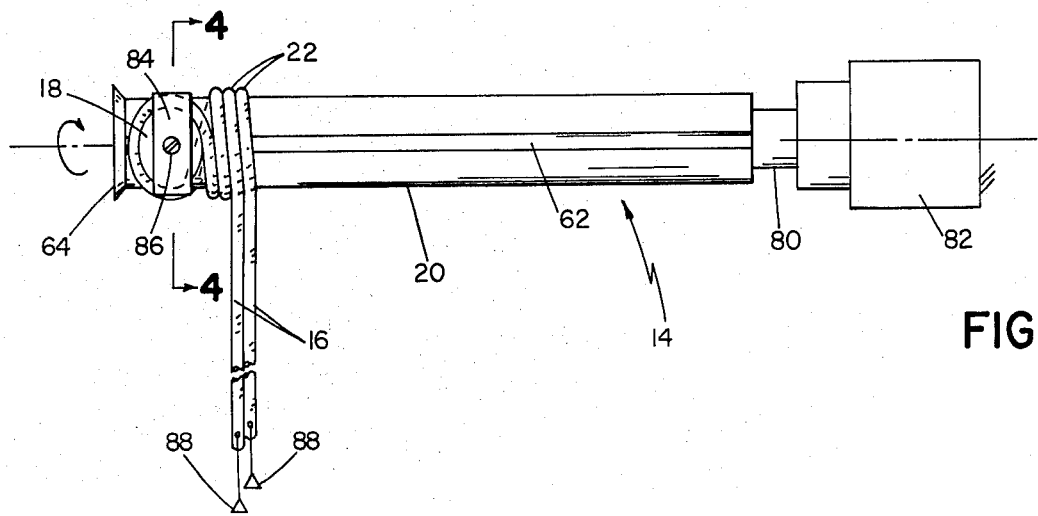

CELL CULTURE DEVICE

The invention described herein was made in the course of work under a grant or award from the Department of Health, Education, and Welfare.

FIELD OF THE INVENTION

This invention relates to cell culture devices for medical use, such as a prosthesis which can be substituted for the endocrine pancreas.

BACKGROUND OF THE INVENTION

Prior cell culture devices have used three dimensional polymeric matrices comprising bundles of parallel fibers potted together at each end to form artificial capillary beds. See, e.g., Knazek et al. U.S. Pat. No. 3,821,087.

Spielberg Canadian Pat. No. 1,027,304 shows an artificial gland, in which a single blood flow path is defined by a semipermeable membrane coiled in a flat spiral. Devices such as that disclosed in the Spielberg have undesirably long response times when used, e.g., as an artificial pancreas, because of the great diffusion distances between the cell culture and the blood flow path.

Prior efforts of the present invention on both parallel and coiled devices are described in Chick et al., *A Hybrid Artificial Pancreas*, Vol. XXI Trans.Amer.Soc.Artif.Int. Organs, 1975 and Whittemore et al., *Effects of the Hybrid Artificial Pancreas in Diabetic Rats*, Vol. XXIII Trans.Am.Soc. Artif.Intern.Organs, 1977.

SUMMARY OF THE INVENTION

The invention provides a cell culture device which avoids undesirable clotting and which has a short response time. The device is easy to charge with pancreatic cells for use as a reliably effective artifical pancreas.

In one aspect the invention features a cell culture device having a housing, a spool mounted within the housing, the housing and spool defining a fluid tight cavity, and a semipermeable tube wrapped about the spool along its longitudinal axis to form coils in the cavity, the interior of the tube defining a fluid flow path for communicating with a fluid source, and the walls of the housing, spool, and tube defining a cell culture compartment. In preferred embodiments the housing and spool are cylindrical and the spool is coaxially mounted within the housing; the cavity is just wide enough and high enough to provide a snug fit for the coils; adjacent coils touch each other; the housing has a port for charging the compartment with cells and a vent for applying a vacuum to the compartment to draw the cells in from the port during charging; the housing and spool are scored at one end so that the end may be cleanly broken away after use to provide access to the compartment; the tube is wound about a post on the spool to provide two strands which are wrapped together about the spool so that the ends of the tube exit from the same end of the housing to provide for simple attachment to the user; the spool has a shallow thread cut on its surface to facilitate retention of the semipermeable tube during winding and to provide a flow channel to disperse material during cell loading, or it may have longitudinal surface grooves for the latter purpose; and the ends of the tube extend from the housing to form cannulae, each having an external notch for suturing to a vessel.

In another aspect the invention features an inlet and an outlet strand of the semipermeable tube being wrapped to form adjacent alternating coils to provide improved convective transport. In preferred embodiments the tube is wound about a post at one end of a spool to form the inlet and outlet strands, and the strands are wrapped together along the axis of the tube to form the alternating coils.

In yet another aspect the invention features the semipermeable tube being wrapped to form helical coils in the cavity to provide improved convective transport by creating secondary flows in the fluid within the tube, which scour the boundary fluid layer away from the tube walls. In preferred embodiments the tube is wrapped about a circular cylindrical spool coaxially mounted within the housing to form coils no more than ⅜ inch in diameter.

PREFERRED EMBODIMENT

We turn now to the structure and operation of a preferred embodiment, first briefly describing the drawings thereof.

DRAWINGS

FIG. 2 is a partially exploded longitudinal section of the housing of the pancreas of FIG. 1.

FIG. 3 is a longitudinal side elevation, partially in section and broken away, of the spool of the pancreas of FIG. 1.

FIG. 4 is a section through 4—4 of FIG. 7.

FIG. 5 is a perspective view of the inlet and outlet nipple fitting of the pancreas of FIG. 1.

FIG. 6 is a section through 6—6 of FIG. 1.

FIG. 7 is a longitudinal side elevation, somewhat schematic, showing an apparatus for assembling the pancreas of FIG. 1, with the pancreas being shown in an intermediate stage of construction.

STRUCTURE AND METHOD OF CONSTRUCTION

Figure 1:
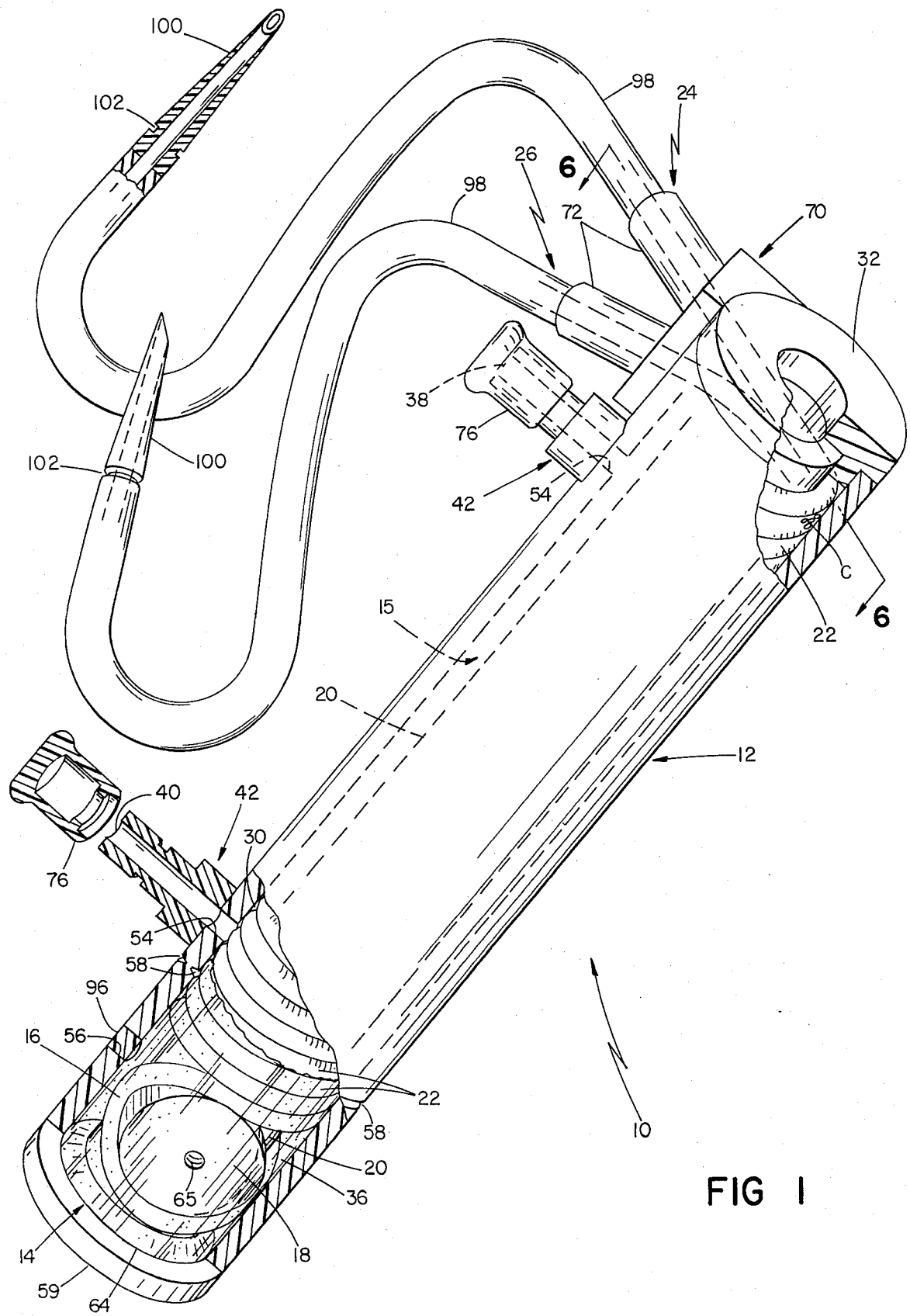
FIG. 1 is an enlarged perspective view, partially in section and broken away, of an artificial pancreas embodying the invention.

There is shown in FIG. 1 an artificial pancreas 10 having a circular cylindrical housing 12, a spool 14 coaxially mounted within the housing to define a fluid tight cavity 15, and a perfusion tube 16 wrapped around a post 18 and a body portion 20 of the spool to form coils 22. One end of tube 16 extends through inlet 24 and the other end through outlet 26 in housing 12.

A cell culture compartment 30 is defined by the inner surface of housing 12, the outer surface of body 20 of spool 14, the walls of tube 16, and the inner ends of collar 32 and plug 36. Cell charging port 38 and vent 40 communicate with compartment 30 through nipples 42.

To prepare housing 12 (FIG. 2), a tangential slot 50 (10 mm long, 3 mm wide) is cut in one end of a transparent polycarbonate tube 52 (70 mm long, ⅜ inch O.D., ¼ inch I.D.), holes 54 and 56 (1.6 mm diameter) are drilled in the sides of the tube, and opposed circumferential grooves 58 are scored on the inner and outer surfaces of the tube 15 mm from its other end. The scored end of tube 52 is sealed with a transparent Plexiglas disc 59 (⅜ inch diameter, 1/16 inch thick), glued to the tube (all "glue" herein is Amicon Epoxy 640).

Turning now to FIG. 3, body 20 of spool 14 is a transparent polycarbonate tube (69 mm long, ⅜ inch O.D., ¼ inch I.D.), having a circumferential groove 60 scored 14 mm from one end and three equally angularly spaced deep grooves 62 cut along its length. A Plexiglas disc 64 (⅛ inch diameter, 1 mm thick) having bevelled edges is glued to the scored end of body 20 to seal it.

Referring to FIGS. 3 and 4, post 18 is a solid Plexiglas rod (⅜ inch diameter) having a threaded hole 65 in the center of one end, and machined at the other end to match the curvature of body 20. The post is glued in position 1.5 mm from disc 64 and milled to protrude 1/16 inch from the surface of body 20.

Turning to FIG. 5, fitting 70 is a block of transparent Plexiglas (16 mm long, 6 mm wide), machines at one end to conform to slot 50 and at the other end to provide two slightly divergent nipples 72 (6 mm long, 3 mm O.D., 1.6 mm I.D., spaced 5 mm center to center at inner ends and 7 mm at outer ends). Similarly (FIG. 6) nipples 72 (6 mm long, 3 mm O.D., 1.6 mm I.D.) are transparent Plexiglas blocks, machined at one end to fit against the outside surface of housing 12, and notched at the other end to receive a stopper 76.

Turning now to FIG. 7, to form helical coils 22, a mandrel 80 is inserted in the open end of spool 14 and fixed horizontally in a chuck driven by a servo-controlled motor 82. The spool is initially positioned with post 18 facing upwardly (the post has been rotated from its initial position in FIG. 7), and a temporary clamp 84 (7 mm wide, arcuate segment of thin Plexiglas tubing) is fastened (FIG. 4) to post 18 by screw 86 inserted in hole 65. Tube 16 (100 cm long, 1.46 mm O.D., 1.10 mm I.D., XM-50 high flux 50,000 molecular weight cut-off material, stabilized by immersion in a 20% glycerin solution, manufactured by Amicon Corporation, Lexington, Massachusetts) is curved about its midpoint to form a U, and inserted under clamp 84, with its ends hanging freely together to one side of the spool. Small weights 88 are fastened to the ends of the tube to provide a slight tension, and the spool is rotated at about 1 rpm, slowly winding both legs or strands of the U together about body 20. Care is taken to assure that adjacent coils 22 touch each other.

After tube 16 is completely wound, clamp 84 is detached, and spool 14 is removed from mandrel 80 and inserted in housing 12, with the ends of the tube extending through slot 50. A Plexiglas collar 32 (5.8 inch O.D., ⅜ inch I.D., 2 mm thick) having circumferential shoulders 92 and 94, is glued to the housing and spool to seal the end of compartment 30 and secure the spool in its concentric position.

The ends of tube 16 are threaded through nipples 72 of fitting 70, and the fitting is glued to housing 12, sealing slot 50.

Nipples 42 are aligned with holes 54 and glued to the housing.

Epoxy is injected with a syringe through hole 56 to form plug 36; care is taken that the plug does not block vent 40. A teflon stopper 96 is glued in hole 56 to seal it.

The spaces between tube 16 and nipples 72 are sealed with epoxy, and silicon rubber sleeves 98 (5 cm long, I.D. approximately equal to the O.D. of tube 16) are swollen in toluene and slipped along the ends of the tube until they abut against the nipples (FIG. 1). When the toluene evaporates, the silicon elastomer forms a tight, yet flexible sleeve which will not kink under the stresses normally applied during handling.

The ends of tube 16 are cut at an angle 15 mm from the ends of sleeves 98, and inserted in a mold (not shown) which is injected with epoxy to form sharp rigid tips 100 having circumferential notches 102.

OPERATION

In use, pancreas unit 10 is sterilized with ethylene oxide and then degassed in a vacuum. A sterile culture medium is flushed through the unit for several days to remove any remaining debris or leachable contaminants. Compartment 30 is then loaded with a suspension C of pancreatic cells and culture medium. Loading is best accomplished by drawing the material into the compartment, from a syringe inserted in charging port 38, with a suction produced by a syringe inserted in vent 40. The material flows on the outer side of the compartment through the space between coils 22 and housing 12. Grooves 62 serve as flow channels to help disperse the material on the inner side of the compartment between coils 22 and spool 14. Port 38 and vent 40 are now sealed with stoppers 76 and the loaded unit is incubated for one week in air with 5% $CO_2$ at 37° C.

The unit is now ready to be mounted by connecting an artery of the user to inlet 24 and a vein to outlet 26. The inlet and outlet are adjacent one another and enter and leave housing 12 from the same direction to allow for easy connection. Tips 100 are used as cannulae for direct insertion, notches 102 providing a means to easily suture the tips to the blood vessels.

The user's blood circulates through semipermeable perfusion tube 16. A rise in the blood glucose level is sensed by the pancreatic cells, causing them to produce insulin, which enters the user's bloodstream through the wall of the semipermeable tube.

In addition to allowing insulin and waste products from the cells to enter the bloodstream the wall of the semipermeable tube also permits the transport of oxygen and essential nutrients from the blood to sustain the cells, and prevents direct contact between cultured cells, leucocytes, and antibodies to provide immunological separation of the cavity and the coils.

The tightly enclosed cell culture compartment, with a minimum of "dead space", provides short diffusion distances between the cells and the bloodstream enabling the device to respond quickly to blood glucose changes.

Convective transport of insulin from the cell culture compartment across the semipermeable perfusion tube (as well as transport of nutrients and oxygen from the bloodstream to the cells) is enhanced due to the closely wound alternating configuration of relatively higher internal pressure coils formed from the inlet half of the tube, and lower pressure coils (because of normal pressure loss) from the outlet half. The resulting pressure differentials cause an increased fluid flux across the walls of the tube and through the cell culture compartment. This effect is maximized adjacent inlet 24 and outlet 26, where the pressure differential is greatest.

Advantageously, the tightly wound coils also promote improved conductive transport by creating secondary flows (due to centrifugal forces) which constantly scour the boundary fluid layer away from the inner surface of the tube, thereby preventing the buildup of insulin at this surface to provide a greater insulin concentration differential across the tube wall.

Should it be desired to evaluate the performance of a unit after a period of use, grooves 58 and 60 permit an end of the the unit to be cleanly broken open to allow easy removal of the culture and perfusion tube matrix with minimum disturbance.

OTHER EMBODIMENTS

Other embodiments are within the following claims. Different perfusion tubing (e.g., larger diameter, thinner wall, different exclusion point) could be used depending on the specific application of each device. For example, larger diameter tubing (e.g., XM-50, 2.40 mm I.D., 2.70 mm O.D., high flux molecular weight cut-off material, manufactured by Amicon) could be used for those applications where clotting is particularly troublesome, or a thinner wall could be used when response time is critical.

The unit has other important applications as well. It could be adapted for use as an artificial liver by loading it with a liver cell suspension. Also, the unit could be used to obtain large quantities of heretofore difficult-to-collect material produced by living cells. For example, it is known that cancer cells produce certain proteins which, until now, have only been obtainable in trace quantities. Large amounts of these proteins could be obtained by loading the cell culture compartment with cancer cells, applying a source of pressurized water and nutrient solution to the inside of the perfusion tube, and opening the vent through a mesh screen; the solution would continually wash through the compartment to flush the protein out the screened vent to a collector.

What is claimed is:

1. A cell culture device comprising,
a housing,
a stationary spool mounted within and wholly surrounded by said housing,
   said housing and spool defining a fluid tight cavity therebetween,
   said housing having a port communicating with said cavity for introduction of cells into said cavity,
   said housing having inlet and outlet means,
a semipermeable tube wrapped about said spool along the longitudinal axis thereof to form coils in said cavity,
   the ends of said tube extending through said inlet and outlet means,
   the interior of said tube defining a fluid flow path for communicating with a fluid source, and
   the walls of said housing, spool, and tube defining an enclosed cell culture compartment,
   said tube being of a material capable of permitting transport, from said compartment to fluid flowing along said path, of products produced by said cells, and transport from said fluid to said compartment of nutrients for said cells, while maintaining immunological separation between said fluid and said cells.

2. The cell culture device of claim 1 wherein, said spool is cylindrical, and the coils of said wrapped tube form a helix.

3. The cell culture device of claim 2 wherein, said housing is a cylinder, and said spool is coaxially mounted within said housing.

4. The cell culture device of claim 1 wherein, adjacent coils of said wrapped tube touch each other.

5. The cell culture device of claim 1 wherein, said housing has a vent communicating with said compartment,
   whereby cells may be drawn into said compartment through said port by suction applied to said compartment through said vent.

6. The cell culture device of claim 1 wherein, said housing and spool are grooved at one end thereof,
   whereby said end may be cleanly broken away to provide access to said compartment.

7. The cell culture device of claim 1 wherein a portion of said tube is curved about a point to form two strands,
   said strands being wrapped together about said spool so that the ends thereof are at the same end of said housing.

8. A cell culture device of claim 7 wherein, said spool has a post at one end thereof, said tube being wound about said post to form said curved portion.

9. A cell culture device of claim 1 wherein, the ends of said tube extend through said inlet and outlet means to the exterior of said housing to form cannulae.

10. A cell culture device of claim 9 wherein, the ends of said tube are notched to provide a means to suture said cannulae.

11. A cell culture device comprising,
a housing having a fluid tight cavity therein,
   said housing having a port communicating with said cavity for introduction of cells into said cavity,
   said housing having inlet and outlet means,
a stationary semipermeable tube mounted in and wholly enclosed by said housing,
   said tube being curved about a transition region to form inlet and outlet portions extending between said region and said means,
   said inlet and outlet portions being wrapped within said cavity to form adjacent coils, with coils formed from said wrapped inlet portion alternating with coils formed from said wrapped outlet portion,
   the interior of said tube defining a fluid flow path for communicating with a fluid source, and
   the walls of said cavity and the exterior of said tube defining a cell culture compartment,
   said tube being of a material capable of permitting transport, from said compartment to fluid flowing along said path, of products produced by said cells, and transport from said fluid to said compartment of nutrients for said cells, while maintaining immunological separation between said fluid and said cells.

12. A cell culture device of claim 11 wherein, said adjacent coils touch each other.

13. A cell culture device of claim 12 wherein, the coils of said wrapped tube form a helix.

14. A cell culture device of claim 11 wherein, said inlet portion and outlet portion are wrapped together along an axis to form said alternating coils.

15. A cell culture device of claim 14, further comprising,
a spool mounted within said housing,
   said tube being wrapped about said spool along the longitudinal axis thereof.

16. A cell culture device of claim 15 wherein said spool has a post at one end thereof,
said tube being wound about said post to form said inlet and outlet portions.

17. A cell culture device of claim 15 wherein said spool is a cylinder.

18. A cell culture device of claim 17 wherein said housing is a cylinder,
said spool being coaxially mounted within said housing.

* * * * *

UNITED STATES PATENT AND TRADEMARK OFFICE
CERTIFICATE OF CORRECTION

PATENT NO. : 4,242,460

DATED : December 30, 1980

INVENTOR(S) : William L. Chick et al.

It is certified that error appears in the above-identified patent and that said Letters Patent are hereby corrected as shown below:

Column 2, line 56, "1/8 inch" should be --5/8 inch--.

Column 2, line 61, "1/8 inch" should be --5/8 inch--.

Signed and Sealed this

Tenth Day of March 1981

[SEAL]

Attest:

RENE D. TEGTMEYER

Attesting Officer  Acting Commissioner of Patents and Trademarks